United States Patent
Niazi

(12) 
(10) Patent No.: US 6,338,862 B1
(45) Date of Patent: Jan. 15, 2002

(54) COMPOSITION AND METHOD OF USE IN TREATING SEXUAL DYSFUNCTION USING CGMP-SPECIFIC PHOSPHODIESTERASE TYPE 5 INHIBITORS

(76) Inventor: Sarfaraz K Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 09/681,362

(22) Filed: Mar. 26, 2001

(51) Int. Cl.$^7$ ................................................ A61K 35/78
(52) U.S. Cl. ........................ 424/728; 424/725; 514/565
(58) Field of Search ................................ 424/728, 725; 514/565

(56) References Cited

U.S. PATENT DOCUMENTS 5,523,087 A * 6/1996 Shlyankevich
6,007,824 A * 12/1999 Duckett et al.

FOREIGN PATENT DOCUMENTS

AU    WO 9965337    *  1/2000

* cited by examiner

*Primary Examiner*—Christopher R. Tate
*Assistant Examiner*—Randall Winston

(57) ABSTRACT

The inhibitors of cyclic guanosine monophosphate (cGMP) phosphodiesterases type 5 (cGMP-PDE5) such as sildenafil citrate (Viagra®) act by increasing the level of cGMP in sexual organs to produce enhanced blood flow and an erectile response of sexual organs. Though sildenafil citrate is a specific inhibitor of cGMP-PDE5, its effects on other body organs produce many side effects including fatalities. Described here is a method of combining cGMP-PDE5 inhibitors with natural sources of nutrients that instantly enhance the levels of endogenous cGMP and thus reduce the therapeutic dose and therefore the side effects of cGMP-PDE5 inhibitors. We have discovered that if sildenafil citrate, as a prototype of cGMP-PDE5, is combined with L-arginine, ginseng, vitamin B6, vitamin B12, and folic acid, all natural and safe ingredients, the dose requirements for sildenafil citrate can be reduced substantially. The specific composition described here assists in the action of sildenafil primarily by increasing the production of cGMP through modulation of nitric oxide pathway (L-arginine→nitric oxide→cGMP) and secondarily by having its own effect on improving blood circulation to sexual organs.

11 Claims, No Drawings

COMPOSITION AND METHOD OF USE IN TREATING SEXUAL DYSFUNCTION USING CGMP-SPECIFIC PHOSPHODIESTERASE TYPE 5 INHIBITORS

DETAILED DESCRIPTION

Adequate sexual function is a complex interaction of hormonal events and psychosocial relationships. The term "sexual dysfunction" generally includes any sexual dysfunction in an animal, preferably a mammal, more preferably a human. The animal can be male or female. Sexual dysfunction may include, for example, sexual desire disorders, sexual arousal disorders, orgasmic disorders and sexual pain disorders. Female sexual dysfunction refers to any female sexual dysfunction including, for example, sexual desire disorders, sexual arousal dysfunction, orgasmic dysfunction, sexual pain disorders, dyspareunia, and vaginismus. The female can be pre-menopausal or menopausal. Male sexual dysfunction refers to any male sexual dysfunction including, for example, male erectile dysfunction and impotence. There are four stages to sexual response as described in the International Journal of Gynecology & Obstetrics, 51(3): 26–77 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, J. Public Health Med., 19(4): 387–391 (1997). In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

The vasculature, which serves erectile tissue in males and females, is similar. In particular, the arterial circulation of the erectile tissues of the genitalia derives from the common iliac artery which branches from the abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery, which supplies the labia pudenda. The internal pudic artery also branches into the artery of the bulb, which supplies the bulbi vestibuli, and the erectile tissue of the vagina. The artery of the corpus cavernosum, another branch of the internal pudic artery supplies the cavernous body of the clitoris. Still another branch of the internal pudic artery is the arteria dorsalis clitoridis, which supplies the dorsum of the clitoris and terminates in the glans and membranous folds surrounding the clitoris, which correspond to the prepuce of the male.

In the male, the internal pudic artery branches into the dorsal artery of the penis (which itself branches into a left and right branch) and the artery of the corpus cavernosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system, which controls blood flow to the penis via the interaction of peripheral nerves associated with the arterial vessels in and around the corpus cavernosum. In the non-aroused or non-erect state, the arteries serving the corpus cavernosum are maintained in a relatively constricted state, thereby limiting the blood flow to the corpus cavernosum. In the aroused state, the smooth muscles associated with the arteries relax and blood flow to the corpus cavernosum greatly increases, causing expansion and rigidity of the penis. Smooth muscle contraction opens valves through which blood can flow from the corpus cavernosum into the extracavernosal veins. When the relevant smooth muscles relax, the valves close diminishing venous outflow from the corpus cavernosum. When accompanied by increased arterial blood flow into the corpus cavernosum, this results in engorgement of the corpus cavernosum and an erection.

While there are obvious differences in the sexual response between males and females, one common aspect of the sexual response is the erectile response. As described in U.S. Pat. No. 5,565,466, the disclosure of which is incorporated herein by reference in its entirety, the erectile response in both males and females is the result of engorgement of the erectile tissues of the genitalia with blood caused by the relaxation of smooth muscles in the arteries serving the genitalia.

Erectile dysfunction is a widespread disorder that is thought to affect about 10% to 15% percent of adult men. A number of causes of erectile insufficiency, in addition to anatomical deficiencies of the penis or scrotum that preclude an erection sufficient for vaginal penetration, have been identified. Causes of erectile dysfunction can be categorized as psychogenic, neurogenic, endocrinologic, drug-induced, or vasculogenic and in any individual suffering from erectile dysfunction there may be more than one cause.

Psychogenic impotence is often the result of anxiety or depression with no apparent somatic or organic impairment. Neurogenic impotence may arise from, for example, surgery or a pelvic injury, involving the nervous system affecting the penis. Erectile dysfunction, which is endocrinologic in origin, is most often associated with the disorders hypo- or hypergonadotropic hypogonadism and hyperprolactinemia.

Vasculogenic impotence is thought to be the most frequent cause of impotence accounting for approximately fifty percent of all cases of organic impotence. In these cases, the erectile dysfunction may be attributed to alterations in the flow of blood to and from the penis. Atherosclerotic or traumatic arterial occlusive disease to the arteries which supply blood to the penis can lead to a decrease in the rigidity of the erect penis as well as increase the time to achieving maximal erection. In still other cases, there is leakage from veins in the penis such that sufficient pressure for an erection can be neither obtained nor maintained.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic, but may be vasculogenic or neurogenic and vasculogenic. About half of diabetic males suffer from erectile insufficiency, and about half of the cases of neurogenic impotence are in diabetics.

Erectile insufficiency is sometimes a side effect of certain drugs, such as beta-antagonists that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection from one to a few times in the patients. Reducing or eliminating such consumption sometimes cures insufficiency due to excessive alcohol consumption.

In the rare cases where the insufficiency is untreatable because of venous leakage, surgery can usually be used to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been used, especially in cases where pharmacological intervention is ineffective, which are usually cases of severe vasculogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory or without potentially severe side effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a phosphodiesterase inhibitor and a smooth muscle relaxant, or phenoxybenzarnine, a non-specific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, causes an erection sufficient for vaginal penetration. The resulting erection is one of significantly shorter duration than that induced by intracavernosal injection of papaverine or phenoxybenzamine and often times is of such short duration that satisfactory sexual relations are difficult or impossible. As an alternative or, in some cases an adjunct to phosphodiesterase inhibition or a-adrenergic blockade for the treatment of erectile dysfunction, prostaglandin E1 (PGE1) has been administered via intracavernosal injection. A major side effect frequently associated with intracorporally delivered PGE1 is penile pain and burning.

DETAILED DESCRIPTION OF INVENTION

Erectile dysfunction is most often attributable to the inability to generate enough NO (nitric oxide) in the corpus cavernosum. The physiologic mechanism of erection of the penis involves release of nitric oxide (NO) in the corpus cavernosum during sexual stimulation. NO then activates the enzyme guanylate cyclase, which results in increased levels of cyclic guanosine monophosphate (cGMP), producing smooth muscle relaxation in the corpus cavernosum and allowing inflow of blood. Compounds that inhibit the breakdown of cGMP (cGMP-PDE5 inhibitors) are thus expected to keep the levels of cGMP elevated for longer period of time and thus act to stimulate sexual function. Several compounds and series of compounds have been identified. For example, the U.S. Pat. No. 6,069,156 to Oku, et al., is for indole derivatives that inhibit cGMP-PDE5. The U.S. Patent to Macor, et al., is for quanazolinone as specific inhibitors of cGMP-PDE5. The U.S. Pat. No. 5,981,527 to Daugan, et al., is for a series of tetracyclic derivatives as inhibitors of cGMP-PDE. One of the most well-known cGMP-PDE5 inhibitor is Viagra®, which is the citrate salt of sildenafil, designated chemically as 1-[[3-(6,7-dihydro-1-methyL-7-oxo-3-propyL-1H-pyrazolo[4,3-d]pyrimidin-5-yl)-4-ethoxyphenyl]sulfonyl]-4-methylpiperazine citrate. Sildenafil has no direct relaxant effect on isolated human corpus cavernosum, but enhances the effect of nitric oxide (NO) by inhibiting phosphodiesterase type 5 (PDE5), which is responsible for degradation of cGMP in the corpus cavernosum. When sexual stimulation causes local release of NO, inhibition of PDE5 by sildenafil causes increased levels of cGMP in the corpus cavernosum, resulting in smooth muscle relaxation and inflow of blood to the corpus cavernosum. Approved by the U.S. FDA on Mar. 27, 1998 for use in humans, Viagra® has been dispensed to millions of patients wherein it proves effective in 7 out of 10 men in controlled clinical trials. The widespread use of sildenafil has several side effects, many serious. Sidenafil is a "type 5 phosphodiesterase inhibitor" because it is supposed to be selective for the enzyme in the penis only. Other forms of the enzyme are present throughout the body, and the drug's function is different in each of these different parts. Unfortunately, some of those effects involve parts such as the eyes, the salivary glands and the blood vessels. The most important contraindication to taking sildenafil is the use of nitroglycerin medication. Some people take this type of medication for their hearts or blood pressure. Other unwanted effects include: headache, flushing, upset stomach, stuffy nose, urinary tract infection, visual changes, such as mild and temporary changes in blue/green color vision or increased sensitivity to light (in 3% of patents), diarrhea. The Food and Drug Administration has confirmed hundreds of deaths associated with the use of sildenafil, mainly as a cardiac side effect. The side effects in the use of sildenafil are dose-dependent. Since sildenafil is used mostly by older men, who may be more disposed to heart disease, or taking medications that might interact with sildenafil, the risk associated with the use of sidenafil are significantly higher than generally accepted. There is also reported a significant correlation between the dose of sildenafil and its side effects. A large number of compounds are under clinical trial in the U.S. such as IC351 (Cialis®), TA1790 (Vivus) or vardenafil (Bayer) that show greater specificity to type 5 phosophodiesterase and do not interact with phosphosdiesterases in other tissues. Since the patents covering sildenafil citrate also included a method claim whereby inhibition of cGMP-PDE5 inhibition is claimed, the development of other more specific and less toxic compound had been delayed until Nov. 8, 2000 when the UK courts struck down the methods claim held by Pfizer company, the marketer of Viagra®. The worldwide market for Viagra® is supposed to grow to about $3 billion by 2003 and newer claims are being approved by regulatory authorities, most recently, the use of Viagra® in diabetic patients. It is therefore unlikely that introduction of newer, perhaps safer compounds would reduce the use of Viagra®. There is therefore a need to devise or invent techniques whereby a synergistic response to the action of sildenafil would result in a downshift in the dose response curve, reducing the need to administer higher doses of sildenafil.

In this invention, a composition is described, which, enhances the response to cGMP-PDE5 inhibitors like sildenafil by a mechanism that involves increasing the quantity of NO. The NO in turn is acted upon by the enzyme guanylate cyclase, which results in increased levels of cGMP, producing smooth muscle relaxation in the corpus cavernosum and allowing inflow of blood. [Rajfer et al., Nitric Oxide as a Mediator of Relaxation of the Corpus Cavernosum in Response to Nonadrenergic, Noncholinergic Neurotransmission, New. Engl. J. Med., 326(2), pp. 90–4 (Jan. 9, 1992)]. It is noteworthy that NO was until recently not considered to be of any benefit to the life processes of animals, much less human beings. However, studies have proven that this simple compound had an abundance of uses in the body, ranging from the nervous system to the reproductive system. With the total life expectancy of nitric oxide being from six to ten seconds, it is not surprising that it has not been until recently that it was discovered in the body. The compound is quickly converted into nitrates and nitrites by oxygen and water. Yet even its short-lived life, it has found many functions within the body. Nitric oxide enables white blood cells to kill tumor cells and bacteria, and it allows neurotransmitters to dilate blood vessels. It also serves as a messenger for neurons, like a neurotransmitter. Nitric oxide (NO) is a small membrane-permeating free radical. It is synthesized as needed, since it cannot be stored in vesicles. Consequently, regulation of its synthesis is crucial. The formation of NO requires the substrate L-arginine or other amino acids, which are converted by nitric oxide synthase (NOS) to NO and citrulline: NO is inactivated by $Ca_2^+$/calmodulin, by phosphorylation but seems to be activated by a variety of vitamin B complex components including vitamin B6, B12 and folic acid.

NO in vascular regulation couples endothelial and smooth muscle cells. In blood vessels, vascular dilation is initiated by acetylcholine acting at muscarinic receptors on endothelial cells. This initiates IP3 production, $Ca_2^+$ release from endoplasmic reticulum and activation of NO synthase by $Ca_2^+$/calmodulin. Nitric oxide diffuses to smooth muscle cells and activates guanylyl cyclase. cGMP activates a cGMP-dependent protein kinase which phosphorylates myosin light chain and causes vascular relaxation. [(M. A. Marletta (1993) Nitric oxide synthase structure and mechanism, J. Biol. Chem. 268, 12231–12234; D. S. Bredt and S. H. Snyder (1994) Nitric oxide: A physiologic messenger molecule, Ann. Rev. Biochem. 63,175–195; E. M. Schuman and D. V. Madison (1994) Nitric oxide and synaptic function, Ann. Rev. Neurosci. 17,153–184; J. Garthwaite and C. L. Boulton (1995) Nitric oxide signaling in the central nervous system, Ann. Rev. Physiol. 57, 683–706; M. J. Rand and C. G. Li (1995) Nitric oxide as a neurotransmitter in peripheral nerves: Nature of transmitter and mechanism of transmission, Ann. Rev. Physiol. 57, 659–682; M. B. Kennedy (1994) The biochemistry of synaptic regulation in the central nervous system, Ann. Rev. Biochem. 63, 571–600)].

Supplementation with L-arginine has been shown to be play a role in restoring endothelial-derived nitric oxide production in many disorders in which endothelial-derived nitric oxide is reduced or impaired, including impairment resulting from diabetes and hypercholesterolemia. Studies also point to the role of L-arginine as not only a substrate for NOS in the up-regulation of cGMP, but also acts to reduce cell-mediated breakdown of nitric oxide. [(Creager M A, Gallagher S J, Girerd X J, Coleman S M, Dzau V J, Cooke J P. L-arginine improves endothelium-dependent vasodilation in hypercholesterolemic humans. J Clin Invest October 1992; 90 (4): 1248–1253; Pieper G M, Dondlinger L A. Plasma and vascular tissue arginine are decreased in diabetes: acute arginine supplementation restores endothelium-dependent relaxation by augmenting cGMP production. J Pharmacol Exp Ther November 1997; 283(2): 684–691; Wascher T C, Graier W F, Dittrich P, Hussain M A, Bahadori B, Wallner S, Toplak H. Effects of low-dose L-arginine on insulin-mediated vasodilatation and insulin sensitivity. Eur J Clin Invest Aug. 27, 1997; (8): 690–695; Pieper G M, Siebeneich W, Dondlinger L A. Short-term oral administration of L-arginine reverses defective endothelium-dependent relaxation and cGMP generation in diabetes. Eur j Pharmacol Dec. 19, 1996; 317(2–3): 317–320; Moody J A, Vernet D, Laidlaw S, Rajferj, Gonzalez-Cadavid N F. Effects of long-term oral administration of L-arginine on the rat erectile response. J Urol September 1997; 158(3 Pt 1): 942–947; Wascher T C, Posch K, Wallner S, Hermetter A, Kostner G M, Graier W F. Vascular effects of L-arginine: anything beyond a substrate for the NO-synthase? Biochem Biophys Res Commun May 8, 1997; 234(1): 35–38)].

Presence of NO also enables two rods of sponge-like tissue (the corpus cavernosum and the corpus spongiosum) in the penis to relax thus allowing the inflow of blood to produce an erection. As blood flows through the penile arteries into the penis, the increased pressure compresses the veins that drain blood from the penis, preventing outflow during sexual stimulation. NO operates, similarly, on a woman's clitoris, helping to maintain sexual excitation. If sufficient NO is not produced, erection or sexual stimulation does not occur.

Certain botanical extracts with a long history of use in traditional medicine have been observed to facilitate the conversion of L-arginine into nitric oxide. One observed mechanism for increase in nitric oxide production in endothelial cells is stimulation of the NOS enzyme activity by ginsenosidesa primary active class of ingredient extracted from ginseng that is known to act as antioxidants as well. Ginsenosides (the primary active component of ginseng) have been shown to increase NO production in endothelial cells. One observed mechanism for increase in NO production is up-regulation of NOS activity by ginsenosides. The effects of ginsenosides on NO production has implications for improved sexual function, and may partly account for the aphrodisiac effect of Panax ginseng used in traditional Chinese medicine. [(Chen X. Cardiovascular protection by ginsenosides and their nitric oxide releasing action. Clin Exp Pharmacol Physiol August 23, 1996; (8): 728–732; Han S W, Kim H. Ginsenosides stimulate endogenous production of nitric oxide in rat kidney. Int J Biochem Cell Biol May 28, 1996; (5): 573–580; Chen X, Lee T J. Ginsenosides-induced nitric oxide-mediated relaxation of the rabbit corpus cavernosum. Br J Pharmacol May 1995; 115(1): 15–18)]. It has been shown that RG1, the purified derivative of ginsenoside enhances the production of NO for killing certain tumor cells. [Fan et al., Enhancement of Nitric Oxide Production from Activated Macrophages by a Purified Form of Ginsenoside (Rg1), American Journal of Chinese Medicine, Vol. XXIII, No. 3–4. pp. 279–287 (1995) Institute for Advanced Research in Asian Science and Medicine)]. The ginseng used in this embodiment is preferably, Panax ginseng. However, other forms of ginseng may alternatively be used. Such other forms include, but are not limited to, *Panax quinquefolius, Panax notoginseng, Eleutherococcus senticosus*, and *Acanthopanax senticosus*. The ginseng used in the formulation of the invention should be the dried extract of the root of the plant with a total saponin content of not less than 4.0 percent. B-complex vitamins are important to the activity of hundreds of enzymes and in energy metabolism. Low levels of circulating folate and vitamin B6 confer an increased risk of peripheral vascular disease, leading to potential reduction of erectile function [Robinson K, Arheart K, Refsum H, Brattstrom L, Boers G, Ueland P, Rubba P, Palma-Reis R, Meleady R, Daly L, Witteman J, Graham I. Low circulating folate and vitamin B6 concentrations: risk factors for stroke, peripheral vascular disease, and coronary artery disease. Circulation Feb. 10, 1998; 97(5): 437–443)]. Furthermore, the vitamins added to the composition might also function to enhance the absorption, and/or to enhance the activity of NO synthase.

Several patents have been issued relating to the involvement of L-arginine and the nitric oxide cycle. Some notable discoveries include: U.S. Pat. No. 6,187,744 to Rooney is for methods for time-regulated prophylaxis or treatment of animals or humans for limited circulatory oxygen delivery induced by the inhibitory effects of a plasma-borne hemoglobin-based material on L-arginine X→nitric oxide X→cGMP pathways in the arteriovenous vasculature. The properties of the invention restore and increase circulatory oxygen delivery by increasing circulatory flow of the blood-hemoglobin-based material through selective activation of L-arginine→nitric oxide X→cGMP pathways in the arterial rather than venous vasculature. A method of the invention utilizes oxygen-carrying biocolloid compositions that consist of a hemoglobin-based material and a guanosine 3':5'-cyclic monophosphate (cGMP) generating entity, for treatment of animals and humans in need thereof for diseases or medical conditions which utilize the biocolloids as hemodiluents, blood substitutes, plasma expanders, or resuscitative fluids. The invention provides selective administration of cGMP generating entities for prophylaxis or treatment of animals or humans with limited circulatory oxygen delivery induced by a plasma hemoglobin-based material arising from intravenous administration, disease or medical condition. Most importantly, the invention provides for time-controlled enablement of the oxygen-delivering properties of the invention that would be used for treatment of specific diseases or medical conditions requiring time-dependent increases in circulatory oxygen delivery. The U.S. Pat. No. 6,133,320 to Yallampalli, et al., is for the treatment of osteoporosis and metabolic bone disorders with nitric oxide substrate and/or donors where primary and secondary osteoporosis in a female or a male mammal is treated by administering thereto a nitric oxide synthase substrate, a nitric oxide donor or both, optionally; in further combination with one or more of an estrogen, a progestin, an anabolic steroid. Nitric oxide substrate or donor also can be combined with one or more of other medications acting on bone, such as bisphosphonate, calcitonin, fluoride, androgen and other novel therapeutic agents. Either nitric oxide donor or substrate by itself or combination with other medications as described above can be used in both women and men, (preferably human) for prevention and treatment of osteoporosis and other metabolic bone disorders. The U.S. Pat. No. 5,968,983 to Kaesemeyer is for method and formulation for treating vascular disease where a therapeutic mixture comprised of L-arginine and inhibitors of Hmg—CoA-Reductase is disclosed for the treatment of diseases related to endothelial dysfunction, wherein the endothelial dysfunction is relieved by stimulating the constitutive form of nitric oxide synthase (cNOS) to produce native nitric oxide (NO). The U.S. Pat. No. 5,543,430 to Kaesemeyer is for a method and formulation of stimulating nitric oxide synthesis where a therapeutic mixture comprising a mixture of L-arginine and an agonist of nitric oxide synthase, namely nitroglycerin, is disclosed for the treatment of diseases related to vasoconstriction, wherein the vasoconstriction is relieved by stimulating the constitutive form of nitric oxide synthase (cNOS) to produce native nitric oxide (NO). The native NO having superior beneficial effect when compared to exogenous NO produced by a L-arginine independent pathway in terms of the ability to reduce clinical endpoints and mortality. The U.S. Pat. No. 6,007,824 to Duckett, et al., is for a composition and method for treating sexual dysfunction by natural means using a combination of L-arginine, ginseng and *Zizyphi fructus* in an orally administered dosage. The combination works synergistically to alleviate erectile dysfunction by stimulating enough release of NO in the corpus cavernosum to produce and sustain smooth muscle relaxation, thereby allowing the inflow of blood and alleviating erectile dysfunction. Thus, a natural medicinal alternative to Viagra® is provided for the treatment of erectile dysfunction. The composition and method is also useful in treating sexual conditions in females. The U.S. Pat. No. 6,197,782 to Garvey, et al., discloses nitrosated and/or nitrosylated phosphodiesterase inhibitors having the formula $NO.sub.n$-PDE inhibitor where n is 1 or 2. The invention also provides compositions comprising such compounds in a pharmaceutically acceptable carrier. The invention also provides a composition comprising a therapeutically effective amount of an phosphodiesterase inhibitor (PDE inhibitor), which can optionally be substituted with at least one NO or $NO.sub.2$ moiety, and one to ten fold molar excess of a compound that donates, transfers or releases nitrogen monoxide as a charged species, i.e., nitrosonium ($NO^+$) or nitroxyl ($NO^-$), or as the neutral species, nitric oxide (NO.) or which stimulates endogenous EDRF production. The invention also provides compositions comprising such compounds in a pharmaceutically acceptable carrier. The invention also provides methods for treating sexual dysfunctions in males and females. The U.S. Pat. No. 5,523,087 to Shlynkevich is for a pharmaceutical composition is disclosed for the treatment of diabetic male sexual dysfunction, which comprises: (a) 45 to 60 parts by weight of one or more phytoestrogen compounds calculated as a free aglycon form of isoflavone; (b) 0 to 400, preferably 200 to 300 parts by weight of phosphatidyl choline; (c) 10 to 50 parts by weight of beta-sitosterol; (d) 0 to 300, preferably 30 to 100 parts by weight of Damiana leaf dry extract; (e) 0 to 15, preferably 1 to 3 parts by weight of Vitamin A; (f) 0 to 250, preferably 20 to 100 parts by weight of Vitamin B1; (g) 0 to 300, preferably 50 to 150 parts by weight of Vitamin B6; (h) 0 to 100, preferably 10 to 70 parts by weight of Vitamin E; (i) 0 to 300, preferably 50 to 200 parts by weight of calcium contained in a biologically acceptable calcium salt; (0) 0 to 750, preferably 300 to 500 parts by weight of magnesium contained in a biologically acceptable magnesium salt; and (k) 0 to 100, preferably 10 to 90 parts by weight of zinc contained in a biologically acceptable zinc salt; in admixture with a biologically acceptable inert carrier. The U.S. Pat. No. 6,117,872 to Maxwell, et al., is for enhancement of exercise performance by augmenting endogenous nitric oxide production or activity wherein NO precursors are administered at elevated levels in addition to the diet of the individual to enhance exercise performance. Particularly, L-arginine and L-lysine by enhancing endothelial NO production can provide for greater aerobic capacity and improved exercise performance. The U.S. Pat. No. 5,891,549 to Cooke, et al is for enhancement of vascular function by modulation of endogenous nitric oxide production or activity where vascular function and structure is maintained or improved by long term administration of physiologically acceptable compounds, namely L-arginine, L-lysine, physiologically acceptable salts thereof, and polypeptide precursors thereof, which enhance the level of endogenous nitric oxide or other intermediates in the NO induced relaxation pathway in the host. In or in combination, other compounds, such as $B_6$, folate, $B_{12}$, or an antioxidant, which provide for short-term enhancement of nitric oxide, either directly or by physiological processes may be employed.

It is noteworthy that whereas the value of nitric oxide supplementation is widely recognized and often purported in ameliorating sexual dysfunction, studies that prove instantaneous effects of nutritional, natural supplements in combination with proven cGMP-PDE5 inhibitors have not been reported. The value of long-term nutritional therapy with components known to produce NO is questioned since the half-life of NO is extremely short and no accumulation occurs in the body. The nutritional ingredients purported to enhance NO production in the body to be used alone to ameliorate sexual dysfunction has met little clinical success since they do not offer a time-of-use efficacy as achieved in the use of cGMP-PDE5 inhibitors. Whereas the nutritional ingredients described in this invention are quickly absorbed from the body, a specific proportion and composition is required to obtain optimal uptake from the gastrointestinal tract providing a surge of these ingredients in the tissues. This method is preferred since these components are not stored in the body beyond what is needed for the normal functioning of body metabolism.

According to the present invention, the above-described and other objects are accomplished by providing a combination of cGMP-PDE5 inhibitors with ingredients that enhance their activity. It is further proposed that these components have a short-term effect and in this context, they are not used as dietary supplements or nutritional factors that requires long-term therapy. The specific combination described here therefore provides a higher pharmacological response reducing the need to administer a larger dose of cGMP-PDE5 inhibitors.

Based on research, it is believed that there will be beneficial results for female sexual dysfunction as well, and the composition will likely provide equally beneficial effects to remedy many female conditions. It has been found that clitoral smooth muscle cells include many of the same morphological characteristics as the male corpus cavernosum, and should be physiologically responsive via the same messengers (cGMP) to promote smooth muscle relaxation. Park et al., Morphological/Biochemical Characterization of Human Corpus Clitoral Smooth Muscle Cells in Culture, Journal of Urology, v. 159, n. 5, sup. June 1998). Thus, that which promotes smooth muscle relaxation in the corpus cavernosum, allowing inflow of blood, and alleviating erectile dysfunction in man, should also work well to alleviate female sexual dysfunction. It is, therefore, an object of the present invention to provide a combination of nutritional supplements, natural and organic drugs for the treatment of sexual dysfunction, and for generally increasing sexual performance in both males and females.

It should be understood that the proper relative concentrations of the proposed constituents might vary depending on the physical characteristics and nutritional status of each person. However, it is suggested that the desired effect is best achieved with a single dose of composition comprising the following preferred amounts and known acceptable ranges: sidenafil citrate: 12.5 mg–50 mg (within a range of approximately 10–100 mg) L-arginine: 200 mg (within a range of approximately 100–1000 mg) ginseng: 100 mg (within a range of approximately 50–200 mg), vitamin B6: 100 mg (within a range of approximately 50–250 mg) folic acid: 0.5 mg (within the range of approximately 0.4–10 mg) vitamin B12: 0.75 mg (within the range of approximately 0.5–1.0 mg). The composition described above can be administered orally and thereby provides a safe, convenient remedy for sexual dysfunction. All of the constituents of the composition are available in pure unadulterated form, have been studied intensively for safety and are approved for human consumption by world's major regulatory authorities. Also, the present art of formulation allows inclusion of safe and approved inactive ingredients to formulate a pharmaceutically elegant dosage form containing the above ingredients.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

In its preferred embodiment, three composition containing sildenafil citrate 12.5 mg, 25 or 50 mg containing the same amounts of L-arginine 200 mg, ginseng 100 mg, folic acid 0.5 mg, vitamin B6 100 mg and vitamin B12 0.75 mg were formulated in a capsule dosage form with suitable inert diluents to hide the identity of the product. The composition was administered to 12 subjects age ranging between 40 and 58 years who had been frequent users of Viagra® and free from any diagnosed heart disease or diabetes and were not taking any other medication, except for dietary supplements and vitamins that did not include L-arginine. For the control purpose, Viagra® tablets of 25 mg and 50 mg were used; for the dose of 12.5, half of 25 mg tablet was used; the tablets were crushed and contained in a same size gelatin capsule as the test composition. In a blinded study, the volunteers were given all six products to test on an ad-lib basis. They were informed that the test includes evaluation of two formulations of sildenafil citrate. The volunteers were asked to evaluate the response subjectively whether an adequate, satisfactory erection was achieved.

In its preferred embodiment, three composition containing sildenafil citrate 12.5 mg, 25 or 50 mg, and the same amounts of L-arginine 200 mg, ginseng 100 mg, folic acid 0.5 mg, vitamin B6 100 mg and vitamin B12 0.75 mg were formulated in a capsule dosage form with suitable inert diluents to hide the identity of the product. The composition was administered to 12 subjects who had been frequent users of Viagra®. The age of volunteers ranged from 40–58 years, they were free from any diagnosed heart disease or diabetes, were not taking any other medication, except for dietary supplements and vitamins that did not include L-arginine. For the control purpose, Viagra® tablets of 25 mg and 50 mg were used; for the dose of 12.5, half of 25 mg tablet was used; the tablets were crushed and contained in a same size gelatin capsule as the test composition. In a blinded study, the volunteers were given all six products to test on an ad-lib basis. They were informed that the test includes evaluation of two formulations of sildenafil citrate. At the lowest dose of 12.5 mg, when given alone, only 3 out of 12 subjects reported erection; when given as the composition described, 7 out of 12 subjects reported satisfactory erection. At 25 mg dose 8 out of 12 subjects reported satisfactory erection while 10 subjects reported satisfactory erection at 25 mg dose when given as the composition described. At 50 mg dose the difference was narrowed to 10 subjects reporting erection when given alone and 11 when given as the composition described. It is concluded from this study that using the combination of ingredients as specified in the composition, the required dose of sildenafil to treat sexual dysfunction can be reduced to achieve the same effect as when given alone but at higher does. The most significant advantage appears at lower doses. It is concluded from this study that using the combination of ingredients as specified in the composition, the required dose of sildenafil to treat sexual dysfunction can be reduced to achieve the same effect as when given alone but at higher does.

One of the most significant aspects of this invention is that the combination of ingredients as described above enhances the quality of erection achieved. Thus, whereas the primary design of the invention is reduce the side effects in the use of sildenafil citrate, when taken at higher doses, the quality of response will be enhanced if the patient can tolerate higher doses.

It should be noted that human sexual response is a highly variable phenomenon, subject to development of refractory response to chemical intervention as well as showing high level of variability in its evaluation. Whereas we conclude that the dose of sildenafil citrate can be reduced substantially to achieve the same result, those experienced in the art of treatment would be better able to judge the degree of modification of doses needed to elicit the desired response since the response to these added components would depend also on the general nutritional status of subjects, concurrent administration of nutritional supplements, and a variety of other factors. Nevertheless, any reduction in the dose required to elicit the traditional response to sildenafil citrate will reduce the side effects associated with the use of sildenafil citrate, making it a safer therapy. The same should apply to other cGMP-PDE5 inhibitors that might show side effects because of their effects on other tissues in addition to sexual organs.

What is claimed is:

1. A composition for treating sexual dysfunction comprising effective amounts of an inhibitor of cGMP-specific phosphodiesterase type 5 enzyme, a natural amino acid, ginseng, vitamin B6, vitamin B12 and folic acid.

2. The composition as in claim 1 wherein each of the component of the composition is administered in a separate dosage form.

3. The composition as in claim 1 wherein the inhibitor of cGMP specific phosphodiestrase type 5 is sildenafil citrate or any of its other salt forms.

4. The composition as in claim 1 wherein the natural amino acid is L-arginine.

5. The composition as in claim 1 wherein the natural amino acid is present in the dose range of 100 to 1000 mg.

6. The composition as in claim 1 wherein vitamin B6 is present in the dose range of 50 to 250 mg.

7. The composition as in claim 1 wherein vitamin B12 is present in the dose range of 0.5 to 1.0 mg.

8. The composition as in claim 1 wherein folic acid is present in the dose range of 0.4 to 10 mg.

9. The composition as in claim 1 wherein ginseng represents extract of Ginseng Panax.

10. The composition as in claim 1 wherein ginseng is present in the dose range of 50 to 200 mg.

11. The composition as in claim 1 which consists of:

| | |
|---|---|
| Sildenafil citrate | 25 mg |
| L-arginine | 200 mg |
| Ginseng | 100 mg |
| Vitamin B6 | 100 mg |
| Vitamin B12 | 0.75 mg |
| Folic acid | 0.5 mg |

* * * * *